United States Patent
Bowe et al.

(10) Patent No.: US 7,625,400 B2
(45) Date of Patent: Dec. 1, 2009

(54) STENT WITH ORIENTATION-DEPENDENT PROPERTIES

(75) Inventors: Jason Samuel-Horner Bowe, West Lafayette, IN (US); Thomas A. Osborne, Bloomington, IN (US)

(73) Assignees: Cook Incorporated, Bloomington, IN (US); Med Institute, Inc., West Lafayette, IN (US)

( * ) Notice: Subject to any disclaimer, the term of this patent is extended or adjusted under 35 U.S.C. 154(b) by 101 days.

(21) Appl. No.: 11/593,908

(22) Filed: Nov. 7, 2006

(65) Prior Publication Data

US 2007/0191927 A1    Aug. 16, 2007

Related U.S. Application Data

(60) Provisional application No. 60/734,053, filed on Nov. 7, 2005.

(51) Int. Cl.
*A61F 2/06* (2006.01)
*A61F 2/84* (2006.01)
(52) U.S. Cl. ..................... 623/1.15; 623/1.11
(58) Field of Classification Search ............. 623/1.15, 623/1.16, 1.3, 1.31, 1.22
See application file for complete search history.

(56) References Cited

U.S. PATENT DOCUMENTS

| 5,147,370 | A | 9/1992 | McNamara et al. | 623/1.11 |
| 5,925,061 | A * | 7/1999 | Ogi et al. | 623/1.2 |
| 6,554,848 | B2 * | 4/2003 | Boylan et al. | 606/191 |
| 6,652,579 | B1 | 11/2003 | Cox et al. | 623/1.34 |
| 6,706,061 | B1 | 3/2004 | Fischell et al. | 623/1.15 |
| 2002/0019660 | A1 | 2/2002 | Gianotti et al. | 623/1.15 |
| 2003/0139803 | A1 * | 7/2003 | Sequin et al. | 623/1.16 |
| 2003/0187497 | A1 | 10/2003 | Boylan et al. | 623/1.15 |
| 2004/0002753 | A1 | 1/2004 | Burgermeister et al. | 623/1.15 |
| 2004/0093070 | A1 * | 5/2004 | Hojeibane et al. | 623/1.15 |
| 2004/0230291 | A1 | 11/2004 | Richter | 623/1.15 |
| 2004/0243220 | A1 | 12/2004 | Gianotti et al. | 623/1.15 |

* cited by examiner

*Primary Examiner*—Thomas J Sweet
*Assistant Examiner*—Yashita Sharma
(74) *Attorney, Agent, or Firm*—Brinks Hofer Gilson & Lione

(57) ABSTRACT

A method and device for implantation into a curved vessel is described. The device may be a stent with a generally curved configuration in its radially expanded state. The stent may have a first series of linkages located along a first side of the stent and a second series of linkages located along a second side of the stent. Both series of linkages interconnect structural elements of the stent. During deployment of the stent into a vessel, the second series of linkages undergo longitudinal expansion sufficient to produce a stent having a longer second side than a first side. This difference in longitudinal length between the second side and first side of the stent creates a curved configuration which conforms to the curvature of the vessel which it is implanted into.

22 Claims, 9 Drawing Sheets

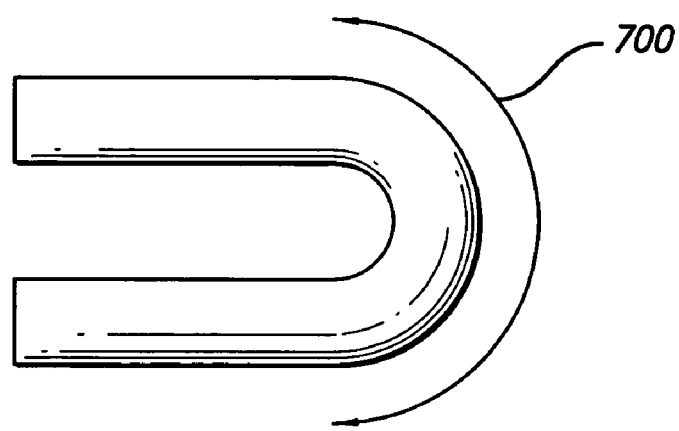
FIG. 7a
FIG. 7b
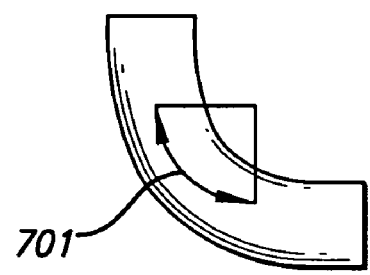
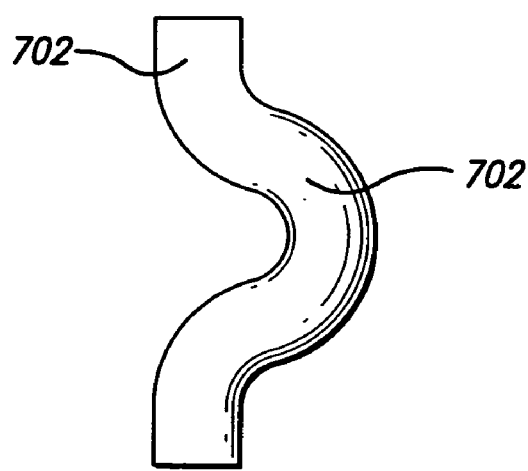
FIG. 7c

STENT WITH ORIENTATION-DEPENDENT PROPERTIES

RELATED APPLICATIONS

This application claims the benefit of priority from U.S. Provisional Application No. 60/734,053, filed Nov. 7, 2005, which is incorporated herein by reference.

FIELD OF INVENTION

The invention generally relates to an implantation device which is curved in a relaxed condition.

BACKGROUND

Stents are typically designed with a generally symmetrical structure to allow the stent to be placed in any circumferential orientation without affecting stent design properties. However, some vessels are generally curved. As a result, implantation of a stent within a generally curved vessel results in loading along a particular direction. Conventional stents that are designed to be placed in any circumferential orientation are generally less capable of incurring loading in a particular direction.

Moreover, some vessels with a general curvature have a tendency to undergo severe bending such that their angle of curvature may continuously change. The portion of the suprafemoral artery (SFA) overlying the knee is an example of a curved vessel which undergoes significant changes in its angle of curvature due to bending of the knee. Stents that are typically straight when deployed will be subject to fatigue from the continuous changes in curvature of the SFA and may ultimately fail. Consequently, a curved stent that can accommodate such continuous bending and therefore adapt to various angles of curvatures within the artery is desirable.

When conventional stents which are straight along their length are deployed within a vessel they exert a continuous radial force on the vessel and attempt to straighten the lumen's original curvature. Therefore, in some cases, it may be desirable to deploy a stent that more closely corresponds to the original curvature of the lumen to avoid trauma and stresses upon the lumen.

In view of the drawbacks of current technology, there is a desire for a stent that can withstand asymmetrical loads incurred from conforming to the curvature of a curved vessel that may bend. Although the inventions described below may be useful in withstanding asymmetrical loads incurred from conforming to the curvature of a curved vessel that may bend, the claimed inventions may also solve other problems.

SUMMARY

Accordingly, an intraluminal device is provided with a curved configuration that is adapted to conform to the curvature of the vessel the intraluminal device is to be implanted within.

The invention may include any of the following aspects in various combinations and may also include any other aspect described below in the written description or in the attached drawings.

In a first aspect, an intraluminal device is provided comprising a tubular structure comprising a plurality of structural elements, said tubular structure having a first end and a second end, a circumference of said tubular structure including a first side and a second side, said first side of said circumference comprising a first pattern of said structural elements and said second side of said circumference comprising a second pattern of said structural elements, said first pattern expandable to a first length between said first end and said second end and said second pattern expandable to a second length between said first end and said second end, said first pattern being different than said second pattern and said first length being shorter than said second length, and wherein said tubular structure in a relaxed condition comprises a curved shape. Preferably, the first side is located about 180° from said second side. Preferably, said first pattern comprises a plurality of first interconnecting members and said second pattern comprises a plurality of second interconnecting members corresponding to said first interconnecting members. Preferably, each of said second interconnecting members comprises a length at least 1% greater than said first interconnecting members. Preferably, each of said first interconnecting members has a first solid link and each of said second interconnecting members has a second solid link, wherein said first solid link and said second solid link are straight in a compressed configuration. Preferably, said first pattern forms an inner radius of curvature of said curved shape, and said second pattern forms an outer radius of curvature of said curved shape. Preferably, wherein a bent configuration in said device includes a compound curve, a three-dimensional curve, or multiple bends.

In a second aspect, a series of structural elements extending in an axial direction around a circumference including a first side and a second side, said structural elements being interconnected by a series of first linkages and second linkages, said first linkages corresponding to said second linkages, said first linkages being disposed along said first side of said circumference and said second linkages being disposed along said second side of said circumference, said series of structural elements including a first end and a second end, wherein said first linkages are shorter in length than said second linkages, and wherein said structural elements in a relaxed condition comprise a curved configuration. Preferably, wherein said series of structural elements comprise a series of peaks and valleys, said first linkages being connected to adjacent peaks and said second linkages being connected to adjacent valleys, and where said first side forms an inner radius of curvature of said curved configuration and said second side forms an outer radius of curvature of said curved configuration. Preferably, wherein at least one of said first linkages and said second linkages comprise flexible portions that bend when said structural elements are in a straight configuration and partially straighten when said structural elements are in said curved configuration. Preferably, wherein said series of structural elements includes at least one radiopaque marker visually indicative of a radial orientation of the device. Preferably, wherein each of said first linkages comprises a fixed length linkage and each of said second linkages comprises a collapsible, flexible linkage, wherein said collapsible, flexible linkage when expanded has an extended longitudinal length that is at least 1% greater than said fixed lengths of said first linkages.

In a third aspect, a plurality of z-stents sequentially connected along a longitudinal axis to form a tubular structure, said plurality of z-stents including a first side and a second side, wherein said plurality of z-stents are interconnected by a series of first linkages and second linkages, said first linkages being disposed along said first side, and said second linkages being disposed along said second side, wherein said tubular structure forms a curved configuration when said second linkages are greater in length than said first linkages in an expanded condition. Preferably, wherein said first linkages are connected to adjacent peaks of the plurality of z-stents.

Preferably, wherein said second linkages are connected to adjacent valleys of said plurality of z-stents. Preferably, wherein said second side of said plurality of z-stents has a longitudinal length greater than that of said first side of the plurality of z-stents in said expanded condition. Preferably, wherein each of said series of first linkages includes a first length and each of said series of second linkages includes a second length, said first length being shorter than said second length.

BRIEF DESCRIPTION OF THE DRAWINGS

Embodiments will now be described by way of example with reference to the accompanying drawings, in which:

FIGS. 7a-f are various stent geometries having various bends along its length in accordance with principles of the embodiments.

DETAILED DESCRIPTION OF THE PREFERRED EMBODIMENTS

Figure 1:
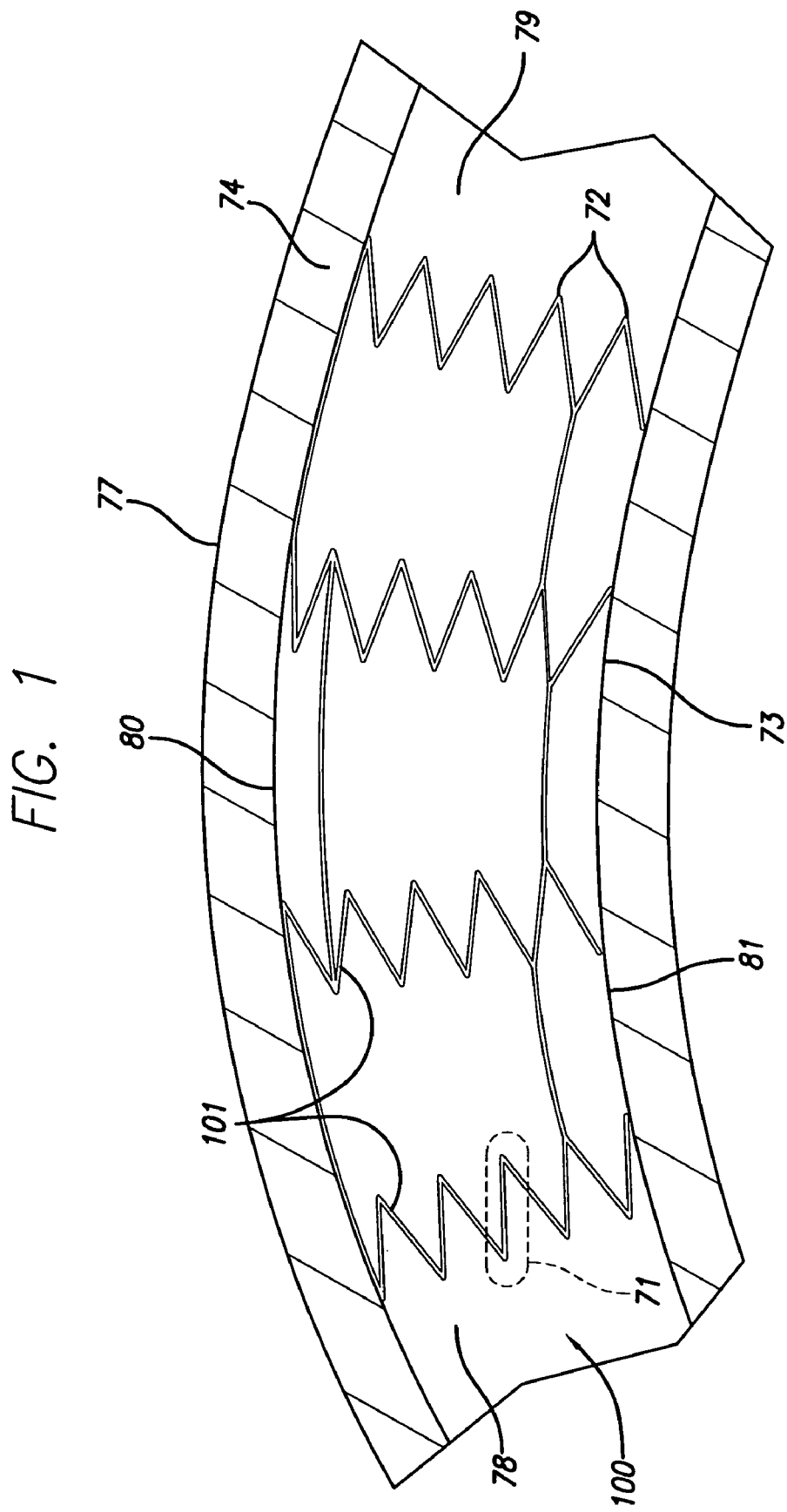
FIG. 1 is a cross-sectional view of a curved stent implanted in a curved blood vessel.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

The invention as generally described herein is directed to intraluminal devices, such as stents, stent grafts, filters, and the like. However, for purposes of clarity, the drawings and description are directed to the preferred embodiment of a stent. However, it should be understood that the invention may also apply to other intraluminal devices.

An exemplary curved stent is shown in FIG. 1. FIG. 1 is a cross-sectional view showing a curved stent 100 implanted within a curved lumen of a blood vessel 77. Although FIG. 1 shows the stent 100 implanted into a blood vessel 77, the stent 100 may be implanted into any vessel having a curved configuration. The curvature of the stent 100 is defined by an outer radius of curvature 74 and an inner radius of curvature 73. The curvature of the stent 100 is configured to correspond to the curvature of the blood vessel 77. The stent 100 is a tubular structure which forms a generally curved shape in its relaxed condition. The stent 100 comprises structural elements 101 having a zigzag configuration. The structural elements 101 extend from a first end 78 to a second end 79 and from a first side 81 to a second side 80. Although FIG. 1 shows zigzag structural elements, any shaped structural element would be apparent to one of ordinary skill in the art and be within the scope of the embodiment. The structural elements extending along the second side 80 form the outer radius of curvature 74 and the structural elements extending along the first side 81 form the inner radius of curvature 73. The second end 79 of the stent 100 may have normal circular radiopaque markers 72 while the first end 78 of the stent 100 may have radiopaque orientation markers, such as J-shaped markers 71. J-shaped markers 71 possess unique directional indicia to assist a physician in recognizing the orientation of the stent 100 when viewed in a two-dimensional screen such as a fluoroscope. The J-shaped markers 71 are visually indicative of a radial orientation of the stent 100. The makers 71 indicate the orientation of the stent 100 prior to and after its deployment, thereby allowing the physician to rotationally position the stent 100 such that its curvature or bend corresponds to the curvature or bend of the blood vessel 77.

Alternatively, the radiopaque marker may comprise a single elongated marker on an end of a side of the stent 100. The elongated marker may be aligned with the curvature of the vessel 77. Alternatively, multiple markers may extend along one side of the stent 100 and may be configured to align with the curvature of the vessel 77. The markers may be positioned at the apices of the struts of the stent 100. Such positioning of the multiple markers may be suitable for determining orientation of the stent 100 within a vessel having compound or multiple curves. The single elongated and multiple markers are visually indicative of a radial orientation of the stent 100. The markers can be created with current marker riveting techniques as known to one of ordinary skill in the art.

Figure 2:
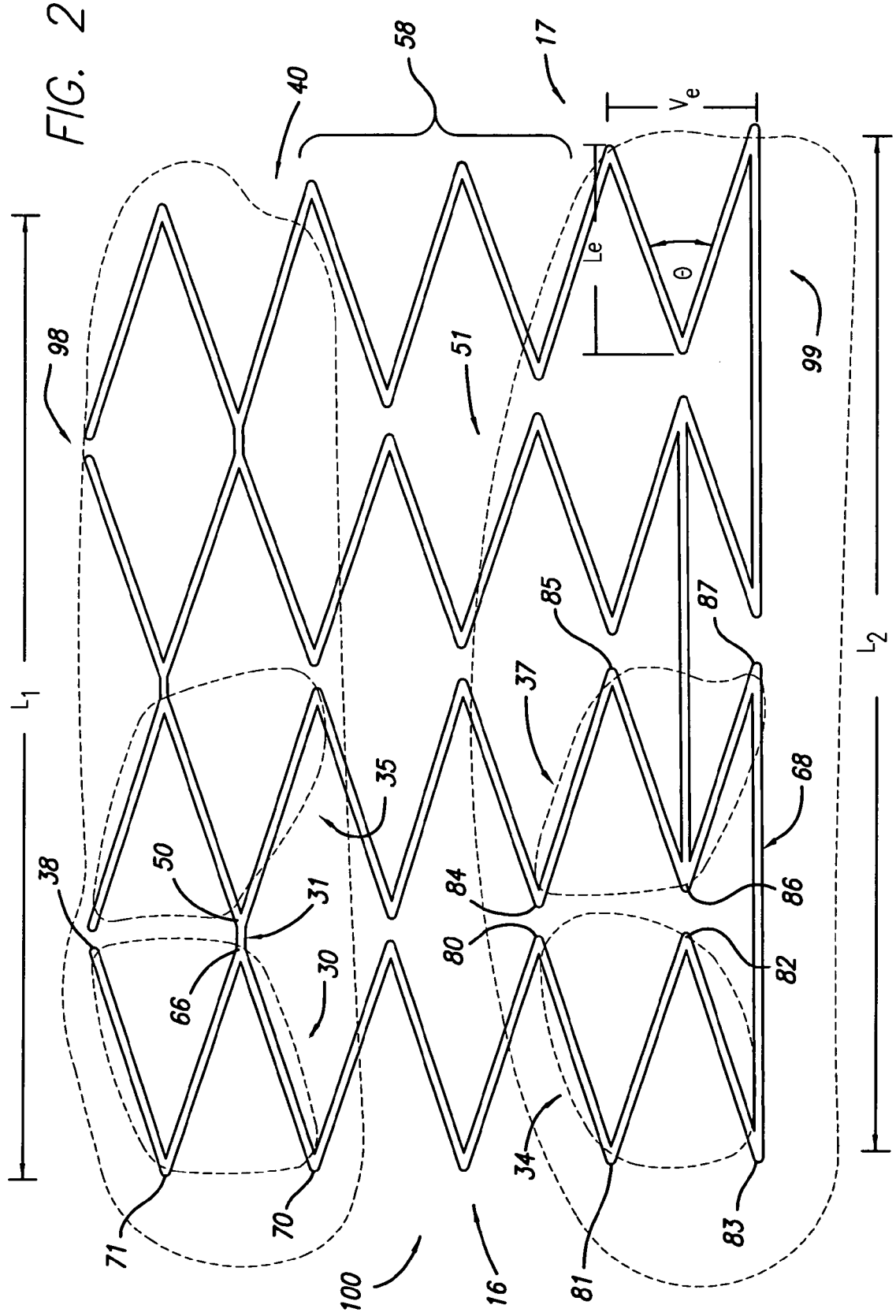
FIG. 2 is a partial flat layout view of a curved stent in an expanded state with solid fixed length linkages along both a first side and second side of the stent.

FIG. 2 is an embodiment showing a cylindrical stent 100 that is unrolled for illustration purposes in its expandable state. Expandable includes self expandable and balloon expandable stents. Only a portion of the unrolled stent 100 is shown in FIG. 2. As shown in FIG. 2, the stent 100 is a tubular structure in which a series of structural elements extend from a first end 16 to a second end 17 and from a first side 98 to a second side 99. The structural elements may be axially aligned with respect to each other.

Structural element 30 has three members arranged in a zigzag "Z" shape. Structural element 30 comprises a total of four apices. Specifically, structural element 30 is defined by peaks 38 and 66 and valleys 70 and 71. Peak 66 of structural element 30 is connected to peak 50 of structural element 35 to form a peak-to-peak link 31.

Structural element 35, similar to structural element 30, contains two peaks and two valleys. Structural elements 35 and 30 may be aligned with no offset such that the valleys 70 and 71 of structural element 30 are not nested within the peaks of structural element 35 to form a packed configuration. Structural element 35 may be configured to appear as a mirror image of structural element 30, as shown in FIG. 2.

Still referring to FIG. 2, a series of peak-to-peak links, such as the peak-to-peak link 31, extend from the first end 16 to the second end 17 to create a first pattern 40 extending along the first side 98 of the stent 100. When the stent 100 expands in the radial direction, as is shown in FIG. 2, the first pattern has a longitudinal length of $L_1$.

Structural element 34 has three members arranged in a zigzag Z shape. Structural element 34 comprises a total of four apices. Specifically, structural element 34 is defined by peaks 80 and 82 and valleys 81 and 83. Structural element 34 is identical to structural element 30 such that both may be superimposed on each other. Valley 83 of structural element 34 is connected to valley 87 of structural element 37 to form a valley-to-valley linkage 68. The peak-to-peak linkage 31 and the valley-to-valley linkage 68 are shown in FIG. 2 as solid links.

Structural element 37 is similarly oriented to structural element 35 and contains two peaks 84, 86 and two valleys 85, 87. Structural elements 37 and 34 are aligned with no offset. Structural element 37 may be configured to appear as a mirror image of structural element 34, as shown in FIG. 2.

Still referring to FIG. 2, a series of valley-to-valley links, such as the valley-to-valley link 68, extend from the first end 16 to the second end 17 to create a second pattern 51 extending along the second side 99 of the stent 100. When the stent 100 expands in the radial direction, as is shown in FIG. 2, the second pattern has an overall longitudinal length of $L_2$.

Because the overall longitudinal length $L_2$ of pattern 51 is greater than the overall longitudinal length $L_1$ of pattern 40, the stent 100 has a tendency to form a curved configuration when it radially expands within a vessel (FIG. 1). The series of valley-to-valley linkages that create pattern 51 preferably form the outer radius of curvature 74 (FIG. 1). The series of peak-to-peak linkages that create pattern 40 preferably form the inner radius of curvature 73 (FIG. 1).

Figure 3:
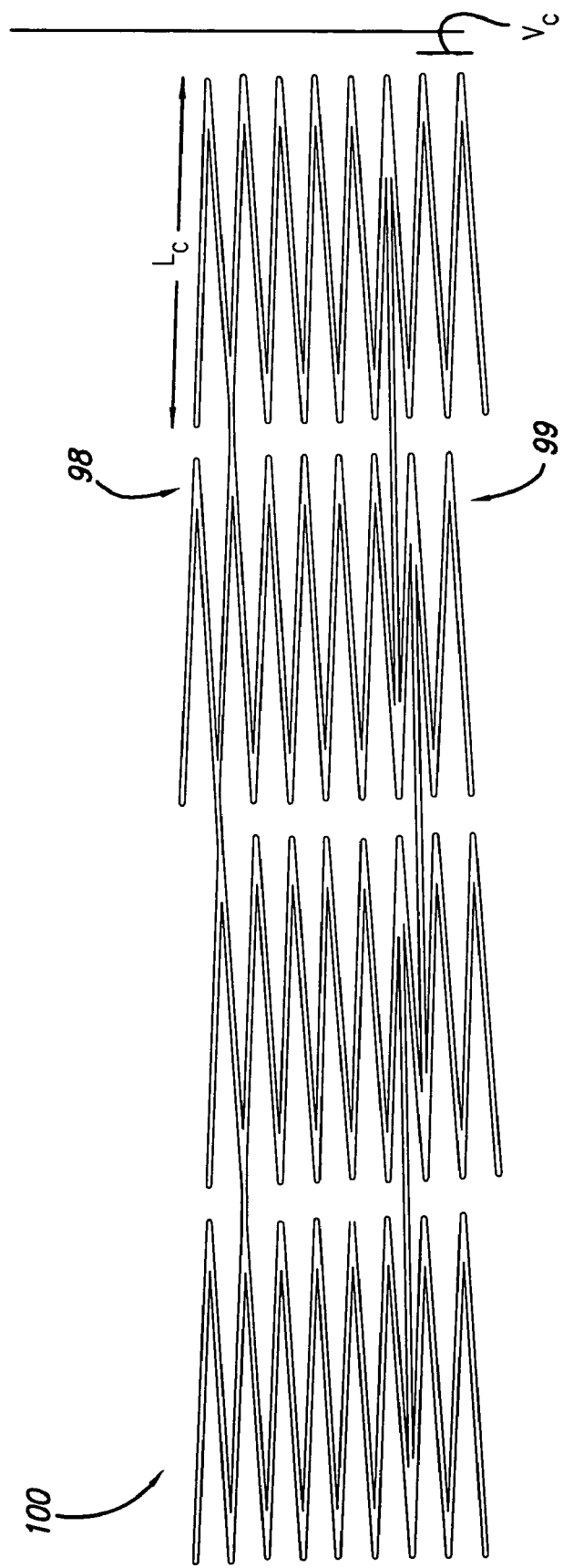
FIG. 3 is a partial flat layout view of a curved stent in a compressed state.

During the expansion process, the angular separation between strut members of a Z-shaped structural element (i.e., the included angle of the valleys), $\theta$, increases relative to the angular separation between strut members in the compressed state (FIG. 3). As a result, the separation between adjacent Z-shaped structural elements with valley-to-valley linkages (e.g., structural elements 34 and 37) may correspondingly increase. The distance between adjacent Z-shaped structural elements with peak-to-peak linkages (e.g., structural elements 30 and 35) may remain the same. This difference in longitudinal length associated with the patterns 40 and 51 that peak-to-peak linkages and valley-to-valley linkages are respectively disposed within causes the stent 100 to attain a curved configuration. This curved configuration allows the stent 100 to have desired unidirectional properties. Unidirectional properties allow the stent 100 to withstand asymmetrical loading which can potentially cause fatigue and eventual failure of the stent 100, as is commonly incurred in curved vessels.

The side elements 58 are the structural elements that are disposed between patterns 40 and 51. The side elements 58 may possess linkages of a length that allows adjacent z-shaped side elements 58 to possess a separation distance that is intermediate between that of adjacent structural elements connected with peak-to-peak linkages and that of adjacent structural elements connected with valley-to-valley linkages. Alternatively, the side elements 58 may not possess linkages, as shown in FIG. 2. An absence of linkages within this region allows unidirectional bending of the stent 100 to occur, thereby allowing the desired curvature of the stent 100 to form when it radially expands.

FIG. 3 illustrates the stent 100 unrolled for illustration in a compressed state. The stent 100 may be in the compressed state when mounted onto a delivery catheter system prior to deployment at a target site. As FIG. 3 shows, the first side 98 and second side 99 of the stent may be identical in length when the stent 100 is radially compressed. Therefore, the overall shape of the stent 100 may be substantially straight before implantation. Thus, the linkages do not prevent the stent 100 from attaining a linear shape in its compressed state. The linkages 31 and 68, shown in FIG. 2, may bend to allow the stent 100 to compress and have a linear shape suitable for advancement within a delivery catheter, which will be discussed below. In the compressed state, the distance between adjacent apices of each of the structural elements, $L_c$ (FIG. 3), is relatively greater than the horizontal distance between adjacent apices in the expanded state, $L_e$ (FIG. 2). Additionally, the vertical distance between apices of each of the structural elements in the compressed state, $V_c$ (FIG. 3), is relatively less than the vertical distance between apices in the expanded state, $V_e$ (FIG. 2).

Figure 4:
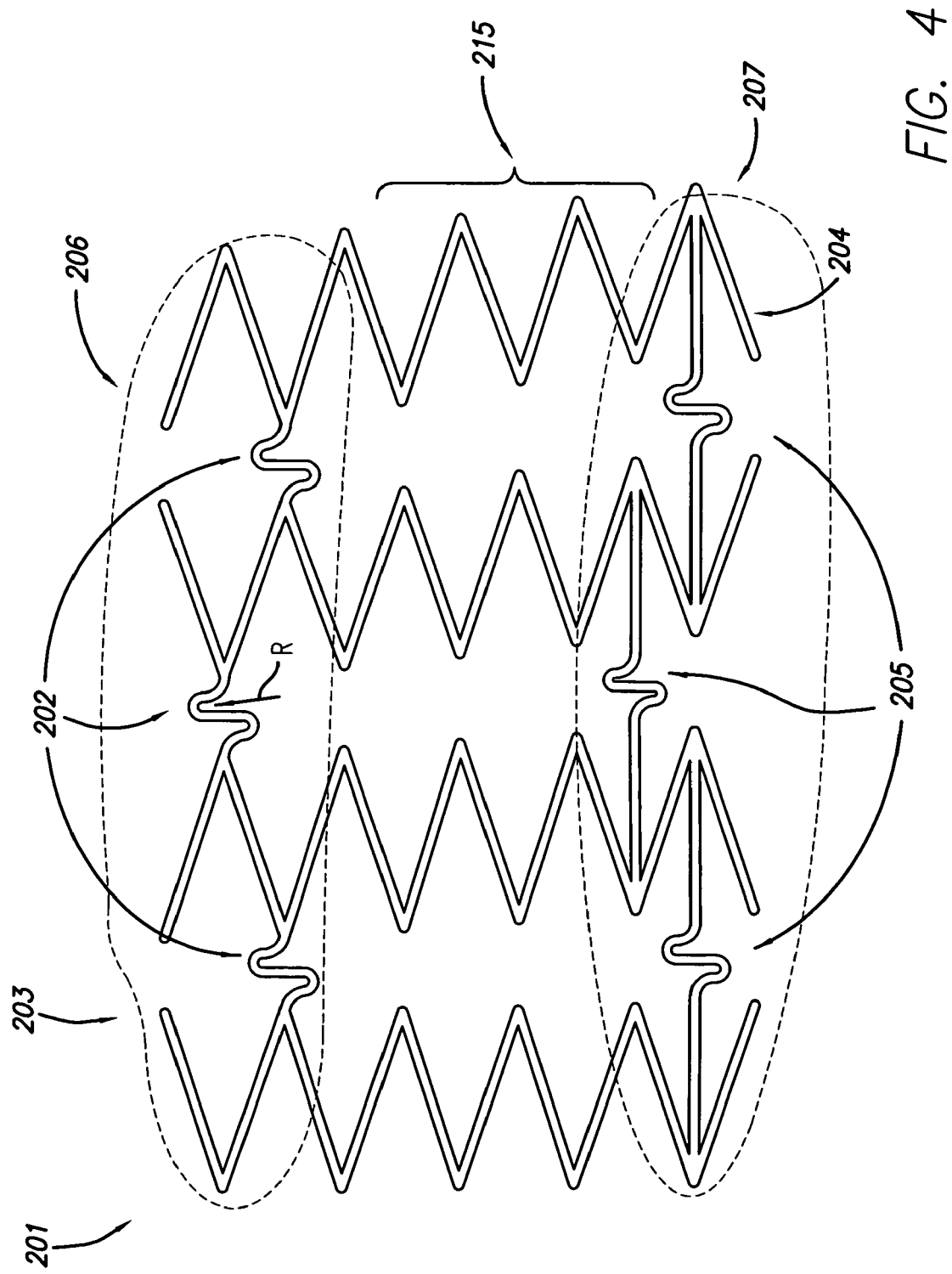
FIG. 4 is a partial flat layout view of a curved stent having flex linkages along both a first side and a second side of the curved stent.

FIG. 4 is a partial flat layout view of an unrolled section for illustration of a stent 201 having flex linkages. The stent 201 is shown in its expanded state which it attains when deployed into a vessel. FIG. 4 illustrates peak-to-peak flex linkages 202 extending along a first side 203 of the stent 201 to form a first pattern 206. Valley-to-valley flex linkages 205 extend along a second side 204 of the stent 201 to form a second pattern 207. Side structural elements 215 are disposed between the first pattern 206 and the second pattern 207. Preferably, side structural elements 215 are not connected by flex linkages in order to facilitate unidirectional bending of the side structural elements 215. Having a series of peak-to-peak flex linkages 202 along the first side 203 and a series of valley-to-valley flex linkages 205 along the second side 204 causes the longitudinal length of the stent 201 to be greater along the second side 204. This difference in length causes the stent 100 to have a tendency to form a curved configuration when it radially expands within a vessel (FIG. 1). The series of valley-to-valley flex linkages may form the outer radius of curvature 74 (FIG. 1). The series of peak-to-peak flex linkages may form the inner radius of curvature 73 (FIG. 1).

Still referring to FIG. 4, R is the radius of the flex linkages 202 and 205. R may be varied to achieve the degree of flexibility desired in a curved vessel. For example, R may be increased for curved vessels having severe bending. A large radius R facilitates asymmetrical loading. A large radius is also suitable for lumens where there is not only a curvature, but the curvature changes due to body movement, as with the SFA portion located over the knee. R may be decreased for curved vessels where the curvature is relatively constant. A variety of factors may be considered in determining a suitable radius, including the vessel the stent 201 is to be implanted into, the severity of bending of the vessel, and the frequency, if any, at which the curvature of the vessel bends and changes. Determining a suitable radius of flexed linkages 202 and 205 for a particular curved vessel on the basis of such various factors will become apparent to one of ordinary skill in the art.

Because the flex linkages 202 and 205 provide the stent 201 with flexibility, the stent 201 may accommodate the loads incurred from severe bending of a curved body artery, such as the SFA. The section of the SFA over the knee is an example of a blood vessel having a bend that can continuously change due to the bending of the knee. The stent 201 may be able to adapt to continuous changing angles of curvature of the SFA without fatiguing. Typical stents that cannot accommodate such asymmetrical loading may be subject to fatigue and may ultimately fail.

The radius flexed links 202 may also be different than the radius of curvature for flexed links 205. In particular, the radius of flexed links 205 is greater than that of flexed links 202.

Figure 5:
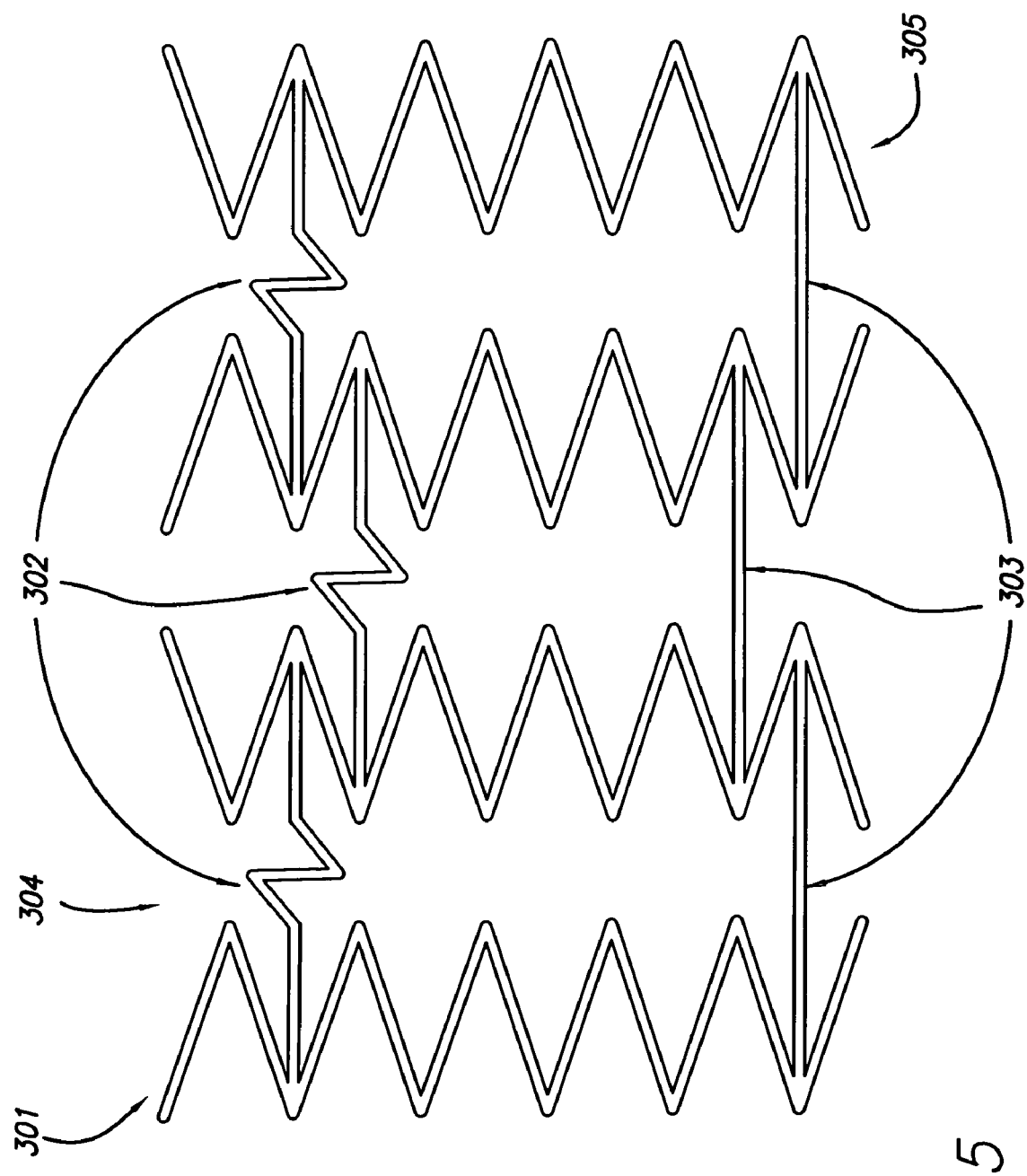
FIG. 5 is a partial flat layout view of a curved stent having valley-to-valley fixed length linkages extending along a first side of the curved stent and valley-to-valley flexed linkages in an unexpanded state and extending along a second side of the curved stent.

FIG. 5 shows a stent 301 with a combination of flex linkages and fix length linkages. FIG. 5 illustrates an intermediate snapshot of the stent 301 undergoing expansion. Each of the z-shaped structural elements is radially expanded. However, the flex linkages 302 are not yet longitudinally expanded. They are still shown in their collapsed configuration. Flex linkages 302 extend along a second side 304 of the stent 301 and fixed solid linkages 303 extend along a first side 305 of the stent 301. FIG. 5 shows that both the flex linkages 302 and the fixed solid linkages 303 connect valleys of adjacent structural elements of the stent 301. Fixed solid linkages 303 may remain constant in length when in both the expanded state and in the collapsed state.

The flex linkages 302 and fixed solid linkages 303 may also be peak-to-peak linkages in which adjacent structural members of the stent 301 are connected to each other at their respective peak points. A difference in overall length may occur when the flex linkages 302 expand from their collapsed state. The pattern created by the series of flex linkages 302 may extend a greater longitudinal length than the pattern created by the series of fixed solid linkages 303. This causes the stent 301 to attain a curved configuration with unidirectional properties. The effect of such a curved configuration is that the stent can conform to the shape of a curved vessel.

Figure 6:
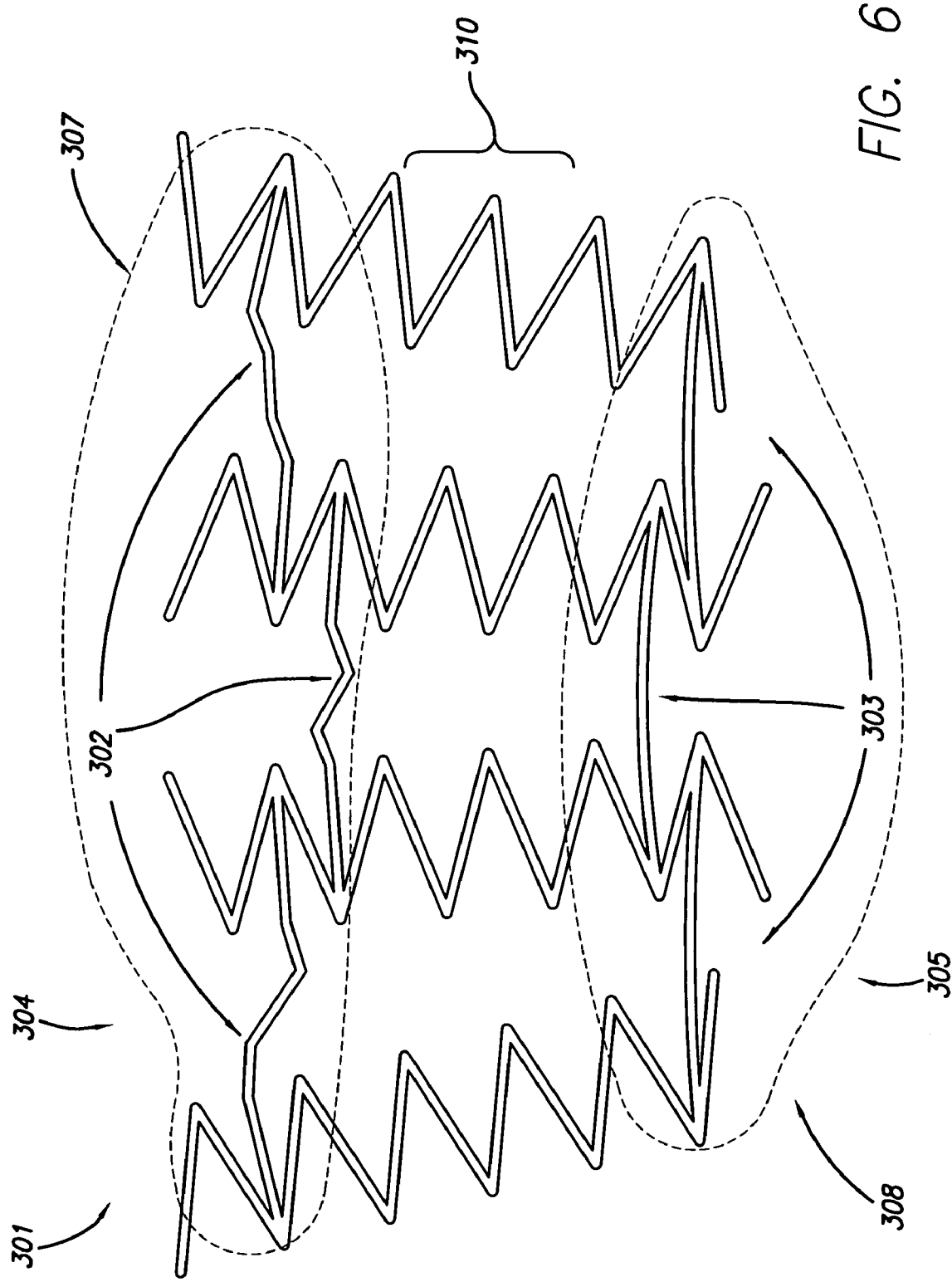
FIG. 6 is a partial flat layout view of the curved stent of FIG. 5 in an expanded state.

FIG. 6 is the unrolled stent 301 with the flex linkages 302 as described in FIG. 5 in the longitudinally expanded condition. This may be the configuration the stent 301 attains when deployed and expanded in an implanted curved vessel. The flex linkages 302 partially straighten in the longitudinal direction when expanded, thereby causing the stent to form a curved configuration. The extent to which the flex linkages longitudinally straighten is dependent upon a number of factors, including the extent of bend or curvature of the vessel and the type of vessel the stent 301 is implanted into. The fixed linkages 303 may remain constant in length. The result is that pattern 307 extends a greater longitudinal length than pattern 308, thereby causing the stent to take a curved configuration when radially expanded. Flex linkages 302 and pattern 307 form the outer radius of curvature 74, shown in FIG. 1. Fixed linkages 303 and pattern 308 form the inner radius of curvature 73, shown in FIG. 1. The expansion process of the stent 301 includes radial expansion of each of the z-shaped structural elements, as shown in FIG. 5, and longitudinal expansion of each of the flex linkages 302, as shown in FIG. 6. Both expansions may occur simultaneously upon deployment into a vessel.

Middle linkages may be present between pattern 307 and pattern 308. The middle linkages may be peak-to-peak linkages in which adjacent side structural elements 310 may be connected at their respective peak points. Alternatively, the middle linkages may be valley-to-valley linkages in which adjacent side structural elements 310 may be connected at their respective valley points. Middle linkages may possess a length proportionally less than the linkages associated with forming the outer radius of curvature 74 and a length proportionally greater than the linkages associated with forming the inner radius of curvature 73.

The arrangement of linkages, as viewed from one of the ends of the cylindrical stent, is now discussed. Referring to FIG. 6, the flex linkages 302 and corresponding pattern 307 that form the outer radius of curvature 74 (FIG. 1) may be oriented at the 12 o'clock position. The fixed linkages 303 and corresponding pattern 308 that form the inner radius of curvature 73 (FIG. 1) may be oriented at the 6 o'clock position. Similarly, in the embodiment of FIG. 2, the valley-to-valley fixed linkages forming pattern 51 may be oriented at the 12 o'clock position while the peak-to-peak fixed linkages forming pattern 40 may be oriented at the 6 o'clock position. In the embodiment of FIG. 4, the valley-to-valley flex linkages 205 forming pattern 207 may be oriented at the 12 o'clock position while the peak-to-peak flex linkages forming pattern 206 may be oriented at the 6 o'clock position. Although not shown, middle linkages may be arranged that have a length proportionally between the length of linkages associated with the outer radius of curvature 74 and inner radius of curvature 73.

Figure 7D:
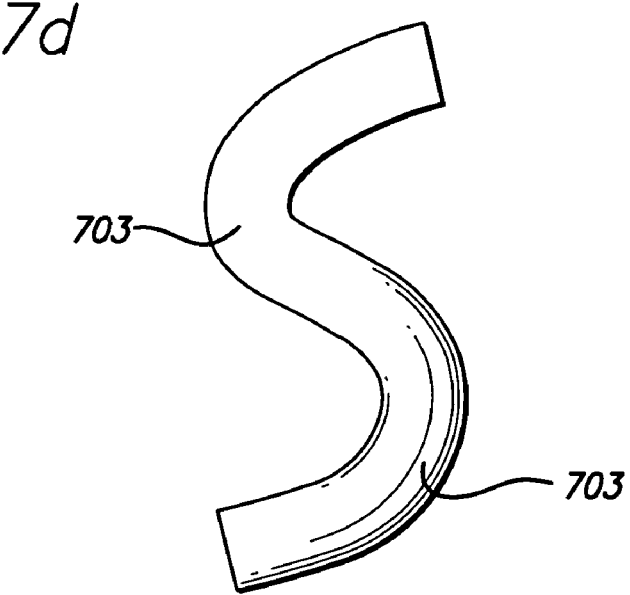
Figure 7E:
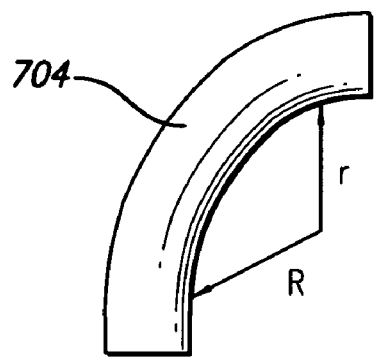
Figure 7F:
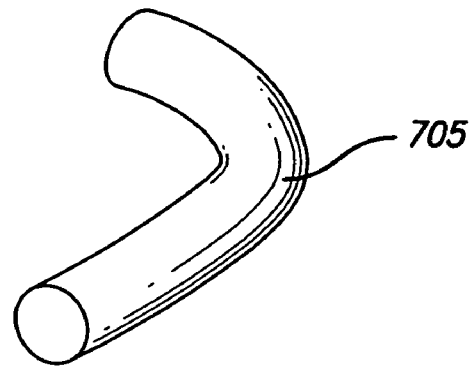

The structural features of the embodiments described above allow stents to be designed with various bends and curves along the length by selectively placing linkages along the circumference of a stent. For example, FIG. 7a shows a stent with a 180° bend 700 along its length. In FIG. 7b, a stent shows a 90° bend 701 along its length. Alternatively, FIG. 8c shows a stent with multiple bends 702 along its length. FIG. 7d also shows a stent with multiple bends 703. FIG. 7e shows a stent having a compound curve 704 in which the compound curve 704 has at least two radii of curvature, r and R. FIG. 7f shows a stent having a bend 705 that extends into three dimensions. In particular the bend occurs along plane x-y, along plane x-z, and along plane y-z. Any and all combinations of the foregoing and other bends and curves known in the art are also contemplated. Selective positioning of the linkages to achieve the bends illustrated in FIGS. 7a-f will be apparent to one of ordinary skill in the art.

The stent of the various described embodiments may be made from a superelastic alloy. Preferably, the superelastic alloy is a nickel-titanium alloy, such as nitinol. Nitinol may undergo a substantially reversible phase transformation that allows it to "remember" and return to a previous shape or configuration. The phase transformation may occur between an austenitic phase and a martensitic phase. The phase transformation may occur by cooling the stent below its phase transformation temperature (shape memory effect). Additionally and more preferably, the phase transformation may occur by applying stress to the stent, thereby stress-inducing martensite in what is known as the superelastic effect. In one example utilizing the superelastic effect, stress may applied to nitinol having an initial shape in the austenitic phase to cause a transformation to the martensitic phase without a change in temperature. A return transformation to the austenitic phase may be achieved by removing the applied stress. In general, superelastic alloys are elastic over a wider range than conventional elastic materials such as stainless steel. For example, nitinol can have an elastic range of up to about 8%.

The embodiments as described herein preferably utilize the superelastic properties of nickel-titanium alloys. By virtue of the superelastic properties of such alloys, the stent tends to naturally spring back to a larger diameter when a restraining stress is removed. Accordingly, the stress introduced into the stent may be released by withdrawing the restraining sheath in a proximal direction away from the stent, whereupon the stent expands to its original, curved shape by transforming back to the austenitic phase.

Preferably, the stent 100 (FIG. 1) may be unitary, meaning that it is constructed from a single piece of material. For example, the stent 100 may be cut to length from stock nitinol tubing. The tubing may then be laser cut to form the desired pattern with the desired linkages. A unitary stent construction avoids process variances of other mechanically linked stents.

Figure 8:
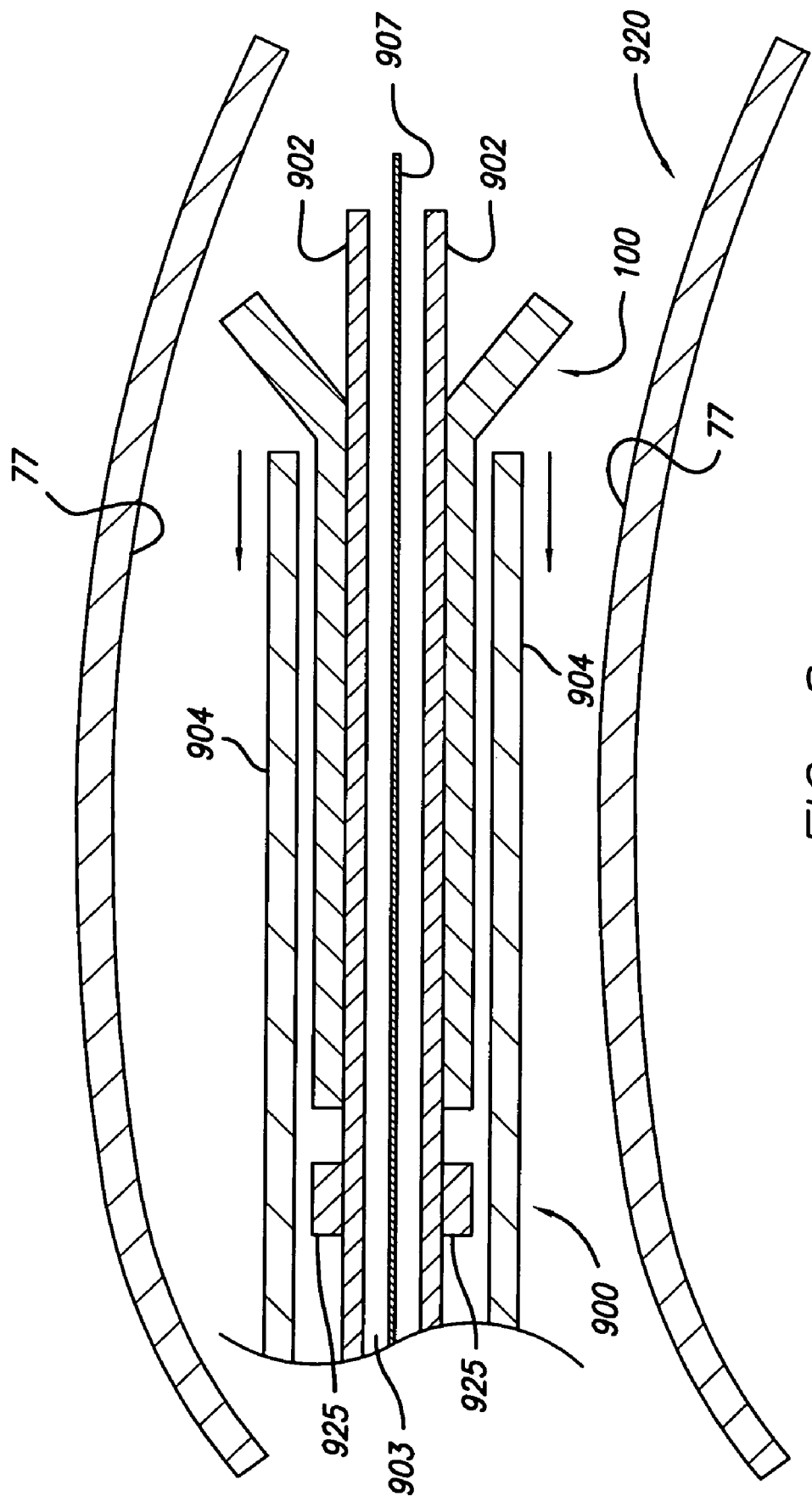
FIG. 8 is a cross-sectional view of a stent collapsed onto a delivery catheter and advanced to an implantation site within a curved blood vessel.

FIG. 8 is a cross-sectional view showing the stent 100 in a collapsed delivery configuration within the delivery catheter 900. The delivery catheter 900 comprises an inner sheath 902. The inner sheath 902 may have a guide wire lumen 903 adapted to receive a guide wire 907. Delivery catheter 900 also includes an outer sheath 904. The outer sheath 904 has a lumen sized for disposal about the inner sheath 902. The outer sheath 904 is retractable and may coaxially slide over inner sheath 902 and stent 100, in order to maintain the stent 100 in the collapsed delivery configuration. The outer sheath 904 maintains a compressive force over the stent 100. As a result, the compressed stent 100 maintains a small profile during delivery to the implantation site 920. Superelastic characteristics of the stent 900 generally allow it to be deformed by collapsing and deforming the stent 100 and creating stress to change to the martensitic phase. Restraining sheath 904 and inner sheath 902 straighten the stent 100 while it is in the delivery configuration, thereby facilitating delivery of the stent 100 to the implantation site 920. Compression of the stent 100 allows the stent 100 to remain in place on the delivery catheter 900 during advancement of the delivery catheter 900. Other means for securing the stent 100 onto the delivery catheter 900 may also be used, such as collars or ridges.

Although the Figures show that each of the peak-to-peak linkages are the same length and each of the valley-to-valley linkages are the same length, the peak-to-peak and valley-to-valley linkages may have varying lengths to achieve greater control of the overall curvature of the stent. For example, referring to FIG. 4, if the valley-to-valley linkages 205 located at the ends are longer than the middle valley-to-valley linkage 205, a larger outer of radius curvature may be achieved along the second side 204 of the stent 201. The valley-to-valley linkages 205 may also increase or decrease in length as one longitudinally moves from the left to the right of the stent 201 of FIG. 4 so as to produce more or less curvature. The ability to alter the radius of curvature of the stent by varying the lengths of the linkages along the first side 203 and second side 204 of the stent 201 may be useful in any curved vessel of the anatomy, including the thoracic aorta. The ability to impart a predetermined curvature to the stent as described herein may also help to minimize any moment or force that is exerted against the curved vessel by the stent.

Although the Figures have shown peak-to-peak and valley-to-valley linkages that are diametrically opposed (i.e., linkages that are parallel with the longitudinal axis of the structure), non-diametrically opposed linkages are also contemplated. Non-diametrically opposed linkages may allow the stent to attain various degrees of curvature. Additionally, a spiral stent configuration may also be possible with non-diametrically opposed linkages.

A method of using the stent 100 within a curved blood vessel 77 is now described. Generally speaking, as shown in FIG. 8, the delivery catheter 900 with the stent 100 disposed thereon in the collapsed configuration is advanced over the guide wire 907 to an implantation site 920 within the curved blood vessel 77. The J-shaped gold markers 71 located on the first end 78 (FIG. 1) of the stent 100 and the normal circular markers 72 located on the second end 79 of the stent facilitate visualization of the alignment and orientation of the stent 100 within the implantation site during and after deployment. The markers 71 and 72 allow the stent 100 to be deployed in a specific orientation in order for the curvature or bend of the stent 100 to conform to the curvature or bend of the blood vessel 77. Longitudinal positioning of the stent 100 may be accomplished by monitoring the markers 71 and 72 on an x-ray screen and orienting the ends of the stent 100, as defined by the J-shaped gold markers 71 and the normal circular markers 72, within the implantation site 920. The implantation site 920 may be fluoroscopically mapped as known by one of ordinary skill in the art.

Radial positioning of the stent 100 may be required in order to rotationally align the curvature of the stent 100 with the curvature of the blood vessel 77. The bend in the stent 100 preferably follows the bend in the vessel 77 upon deployment of the stent 100. It is therefore useful for the physician to know beforehand the location and direction of the bend in the stent 100 prior to deployment such that the outer radius of curvature 74 (FIG. 1) and inner radius of curvature 73 (FIG. 1) of the stent 100 may correspond with the bend of the vessel 77. The J-shaped gold markers 71 have unique directional indicia to assist the physician in such recognition of the desired curved orientation of the stent 100 when viewed in a two-dimensional screen such as a x-ray screen. The J-shaped gold markers 71 may be a solid J-shape. Alternatively, the J-shape gold markers 71 may be formed from discrete markers oriented orthogonally to create the J-shape. Other variations of J-shaped markers are contemplated and are within the scope of this invention.

As an alternative to a stent 100 with normal circular radiopaque markers 72 on its second end 79 and radiopaque orientation markers, such as J-shaped markers 71, on its first end 78, the radiopaque markers may be small rivets composed of a radiopaque material such as gold, tantalum, platinum, or palladium. The markers may be arranged so that there are two markers, one on each end of the stent 100 positioned on the outer radius of curvature 74. Three or more markers may be arranged along the length of the stent 100 on the inner radius of curvature 73. The physician may then orient the stent 100 rotationally using fluoroscopic guidance before deploying the stent 100. The markers may be placed in small eyelets in the stent 100 structure in a manner similar to conventional stents where the markers are used to identify the ends of the stent 100. This arrangement would not only provide rotational information, but also location information regarding the ends of the stent 100.

Once the stent 100 has been radially and longitudinally oriented with respect to the implantation site 920 within the blood vessel 77, the outer sheath 904 of the delivery catheter 900 is gradually retracted with respect to the inner sheath 902, as indicated by the arrows in FIG. 8. Alternatively, the outer sheath 904 may be moved in a proximal direction while simultaneously moving the inner sheath 902 in a distal direction. A holder 925 or other longitudinal restraint that is well known in the art prevents the stent from moving proximally back into the delivery catheter as the outer sheath 904 is proximally withdrawn. The relative movement between the inner sheath 902 and outer sheath 904 may be accomplished by manipulation of control handles located at the proximal end of the delivery catheter 900. Regardless of which method for retracting the outer sheath 904 is used, when the distal end of outer sheath 904 is positioned proximal to the proximal end of the stent 100, as shown in FIG. 8, the stent 100 self-expands to its naturally curved configuration, as shown in FIG. 1. The curvature of the stent 100 conforms to the curvature of the implantation site 920 within the blood vessel 77. After the stent 100 is implanted and contacts the implantation site 920, the delivery catheter 900 and guide wire 907 are withdrawn from the patient's vasculature, completing the procedure.

Although the stents described generally herein are self expanding, the above principles may also be applied to balloon expanding stents. In such embodiments, a balloon expanding in a curved configuration may be useful in forming a stent that expands into a generally curved configuration within a vessel.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An intraluminal device, comprising:
a tubular structure expandable from a compressed condition to an expanded condition, the tubular structure having a first pattern and a second pattern in the compressed condition and the expanded condition, said tubular structure comprising a plurality of structural elements, said tubular structure having a first end and an opposite second end, a circumference of said tubular structure including a first side and a second side, said first side of said circumference comprising a first pattern of said structural elements and said second side of said circumference comprising a second pattern of said structural elements, said structural elements of said first pattern interconnected by a plurality of first interconnecting members, and said structural elements of said second pattern interconnected by a plurality of second interconnecting members, said plurality of first interconnecting members shorter in length than said plurality of second interconnecting members in a predeployed state, said first pattern expandable to a first length between said first end and said second end and said second pattern expandable to a second length between said first end and said second end, said first pattern being different than said second pattern and said first length being shorter than said second length, and wherein said tubular structure in an expanded condition comprises a curved shape.

2. The intraluminal device of claim 1, wherein said first side is located about 180° from said second side.

3. The intraluminal device of claim 1, wherein said first pattern comprises said plurality of first interconnecting members and said second pattern comprises said plurality of second interconnecting members corresponding to said first interconnecting members.

4. The intraluminal device of claim 3, wherein each of said second interconnecting members comprises a length at least 1% greater than said first interconnecting members.

5. The intraluminal device of claim 4, wherein each of said first interconnecting members have a first solid link and each of said second interconnecting members have a second solid link, wherein said first solid link and said second solid link are straight in a compressed configuration.

6. The intraluminal device of claim 1, wherein said first pattern forms an inner radius of curvature of said curved shape, and said second pattern forms an outer radius of curvature of said curved shape.

7. The intraluminal device of claim 6, wherein said bent configuration in said device includes a compound curve, a three-dimensional curve, or multiple bends.

8. The intraluminal device of claim 1, wherein said first side is located about 180° from said second side, wherein said first pattern comprises a plurality of first interconnecting members and said second pattern comprises a plurality of second interconnecting members corresponding to said first interconnecting members, wherein each of said second interconnecting members comprises a length at least 1% greater than said first interconnecting members, wherein each of said first interconnecting members have a first solid link and each of said second interconnecting members have a second solid link, wherein said first solid link and said second solid link are straight in a compressed configuration, and wherein said first pattern forms an inner radius of curvature of said curved shape, and said second pattern forms an outer radius of curvature of said curved shape.

9. An intraluminal device, comprising:
a series of structural elements extending in an axial direction around a circumference including a first side and an opposite second side, said structural elements being interconnected by a series of first linkages and second linkages, said first linkages corresponding to said second linkages, said first linkages being disposed along said first side of said circumference and said second linkages being disposed along said second side of said circumference, said series of structural elements including a first end and a second end, wherein in a predeployed state said first linkages are shorter in length than said second linkages, and wherein said series of structural elements in an expanded condition comprise a tubular structure having a curved configuration.

10. The intraluminal device according to claim 9, wherein said series of structural elements comprise a series of peaks and valleys, said first linkages being connected to adjacent peaks and said second linkages being connected to adjacent valleys, and where said first side forms an inner radius of curvature of said curved configuration and said second side forms an outer radius of curvature of said curved configuration.

11. The intraluminal device according to claim 9, wherein at least one of said first linkages and said second linkages comprise flexible portions that bend when said structural elements are in a straight configuration and partially straighten when said structural elements are in said curved configuration.

12. The intraluminal device of claim 9, wherein said series of structural elements includes at least one radiopaque marker visually indicative of a radial orientation of the device.

13. The intraluminal device of claim 9, wherein each of said first linkages comprises a fixed length linkage and each of said second linkages comprises a collapsible, flexible linkage, wherein said collapsible, flexible linkage when expanded has an extended longitudinal length that is at least 1% greater than said fixed lengths of said first linkages.

14. The intraluminal device of claim 9, wherein said structural elements comprise a series of peaks and valleys, said first linkages being connected to adjacent peaks and said second linkages being connected to adjacent valleys, and where said first side forms an inner radius of curvature of said curved configuration and said second side forms an outer radius of curvature of said curved configuration, wherein said series of structural elements includes at least one radiopaque marker visually indicative of a radial orientation of the device, and wherein at least one of said first linkages and said second linkages comprise flexible portions that bend when said structural elements are in a straight configuration and partially straighten when said structural elements are in said curved configuration.

15. An intraluminal device, comprising:
tubular structure including a first side and an opposite second side, wherein said tubular structure is interconnected by a series of first linkages and second linkages, each of said first linkages being disposed along said first side, and each of said second linkages being disposed along said opposite second side, said second linkages being greater in length than said first linkages in a predeployed condition, and further wherein said tubular structure forms a curved configuration when said second linkages are greater in length than said first linkages in an expanded condition.

16. The intraluminal device of claim 15, wherein said first linkages are connected to adjacent peaks of the tubular structure stents.

17. The intraluminal device of claim 15, wherein said second linkages are connected to adjacent valleys of said plurality of said tubular structure.

18. The intraluminal device of claim 15, wherein said second side of said plurality of expandable stents has a longitudinal length greater than that of said first side of the tubular structure in said expanded condition.

19. The intraluminal device of claim 15, wherein each of said series of first linkages includes a first length and each of said series of second linkages includes a second length, said first length being shorter than said second length.

20. The intraluminal device of claim 15, wherein said first linkages are connected to adjacent peaks of said tubular structure, wherein said second linkages are connected to adjacent valleys of said tubular structure, wherein said second side of said tubular structure has a longitudinal length greater than that of said first side of said tubular structure in said expanded condition, and wherein each of said series of first linkages include a first length and each of said series of second linkages include a second length, said first length being shorter than said second length.

21. The intraluminal device of claim 15, wherein said tubular structure comprises a self expandable stent.

22. The intraluminal device of claim 15, wherein said tubular structure comprises a balloon expandable stent.

* * * * *

UNITED STATES PATENT AND TRADEMARK OFFICE
CERTIFICATE OF CORRECTION

PATENT NO. : 7,625,400 B2
APPLICATION NO. : 11/593908
DATED : December 1, 2009
INVENTOR(S) : Bowe et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this

Twenty-sixth Day of October, 2010

David J. Kappos
*Director of the United States Patent and Trademark Office*